(12) United States Patent
Cusick et al.

(10) Patent No.: US 7,309,339 B2
(45) Date of Patent: Dec. 18, 2007

(54) APPARATUS FOR ALIGNING AN INSTRUMENT DURING A SURGICAL PROCEDURE

(75) Inventors: Michael J. Cusick, Collierville, TN (US); Jens Rüber, Freiburg (DE)

(73) Assignee: Howmedica Osteonics Corp., Mahwah, NJ (US)

( * ) Notice: Subject to any disclaimer, the term of this patent is extended or adjusted under 35 U.S.C. 154(b) by 115 days.

(21) Appl. No.: 10/766,789

(22) Filed: Jan. 27, 2004

(65) Prior Publication Data
US 2005/0021039 A1    Jan. 27, 2005

Related U.S. Application Data

(60) Provisional application No. 60/444,891, filed on Feb. 4, 2003.

(51) Int. Cl.
A61B 17/58    (2006.01)
(52) U.S. Cl. ....................................................... 606/88
(58) Field of Classification Search ................. 606/86, 606/87–89, 79
See application file for complete search history.

(56) References Cited

U.S. PATENT DOCUMENTS

| | | | |
|---|---|---|---|
| 4,488,542 A * | 12/1984 | Helland ........................ 606/59 |
| 4,703,751 A * | 11/1987 | Pohl ............................. 606/62 |
| 4,736,737 A * | 4/1988 | Fargie et al. .................. 606/88 |
| 4,892,093 A | 1/1990 | Zarnowski et al. | |
| 4,952,213 A | 8/1990 | Bowman et al. | |
| 5,342,368 A | 8/1994 | Pettersen | |
| 5,364,401 A | 11/1994 | Ferrante et al. | |
| 5,681,316 A | 10/1997 | DeOrio et al. | |
| 5,788,700 A | 8/1998 | Morawa et al. | |
| 6,090,114 A | 7/2000 | Matsuno et al. | |
| 6,685,711 B2 | 2/2004 | Axelson, Jr. et al. | |
| 6,796,986 B2 * | 9/2004 | Duffner ........................ 606/87 |
| 2002/0198531 A1 | 12/2002 | Millard et al. | |

FOREIGN PATENT DOCUMENTS

FR    2703584    10/1994
FR    2776176    9/1999

OTHER PUBLICATIONS

European Search Report in re: Application No. 04250551, dated May 14, 2004.

\* cited by examiner

*Primary Examiner*—Alvin J. Stewart
(74) *Attorney, Agent, or Firm*—Lerner, David, Littenberg, Krumholz & Mentlik, LLP

(57) ABSTRACT

An apparatus for aligning a cutting instrument during a surgical procedure includes a guide having an elongated slot adapted to receive a cutting instrument for resecting a patient's bone during the surgical procedure. The apparatus includes a translational assembly and first and second rotational assemblies. The translational assembly is coupled to a housing adapted for effecting distal-proximal adjustment of the guide. The first rotational assembly is also coupled to the housing adapted for effecting varus-valgus adjustment of the guide. The first rotational assembly is releasably coupled to the guide. The second rotational assembly is also coupled to the guide and adapted for effecting flexon-extension adjustment of the guide.

49 Claims, 7 Drawing Sheets

APPARATUS FOR ALIGNING AN INSTRUMENT DURING A SURGICAL PROCEDURE

CROSS REFERENCES TO THE RELATED APPLICATIONS

The present application claims priority of U.S. Provisional Application No. 60/444,891, entitled Apparatus for Aligning an Instrument During a Surgical Procedure, filed Feb. 4, 2003, the disclosure of which is incorporated herein by reference.

BACKGROUND OF THE INVENTION

The present invention relates in general to an apparatus for use in aligning medical instruments which are adapted for use during various surgical procedures, and more particularly, to an apparatus for aligning a resection guide for use in arthroplastic surgery of a patient's knee.

Arthroplasty is a known surgical procedure for replacing the knee joint which has been damaged due to disease or trauma. Total knee arthroplasty involves the replacement of portions of the patellar, femur and tibia with an artificial knee prostheses. In particular, a distal portion of the femur and proximal portion of the tibia are cut away, i.e., resected, and replaced with artificial knee components. As use herein, when referring to bones or other body parts, the term "proximal" means closest to the heart and the term "distal" means more distant from the heart.

There are several types of knee prostheses known in the art. One type is commonly referred to as a resurfacing type. In these prostheses, the articular surface of the distal femur and proximal surface of the tibia are resurfaced with respective metal and plastic condylar-type articulate bearing components. The femoral component is often a metallic alloy construction which provides medial and lateral condylar bearing surfaces of multi-radius design of similar shape and geometry as the natural distal femur or femoral-side of the knee joint. The tibial component usually includes a distal metal base component and a proximal interlocking plastic component or insert. The plastic tibial plateau bearing surfaces are of concave multi-radius geometry to more or less match the articular geometry of the mating femoral condyles. These knee prostheses components, which provide adequate rotational and translational freedom, require minimal bone resection to accommodate the components within the boundaries of the available joint space.

The surgical implant of a prosthetic knee joint requires that the distal femur and proximal tibia be prepared to receive the femoral and tibial components by cutting the bone of the femur and tibia to establish accurately located surfaces. Various guides are available to the surgeon for assisting in guiding a medical instrument such as a cutting blade for marking the femoral and tibial cuts which establish the desired resected surfaces. One important feature of these guides is the ability to align the cutting blade accurately when resurfacing the femur and tibia to accommodate the prosthetic knee components. To this end, there is known resection guides suitable for use in total knee arthroplasty from U.S. Pat. Nos. 6,090,114; 5,788,700; and 4,892,093; as well as pending application Ser. No. 09/811,318 entitled Apparatus Used in Performing Femoral and Tibial Resection in Knee Surgery, filed on Mar. 17, 2001, assigned to the same assignee of the present application.

The present invention is specifically directed to an alignment guide intended for any medical condition in which the use of computer-aided surgery may be appropriate, and where a reference to rigid anatomical structures can be identified. More particularly, the present invention is directed to an alignment guide which provides improvements in accurately aligning the cutting blade for resection of bone, for example, the distal femur and proximal tibia during arthroplastic knee surgery.

BRIEF SUMMARY OF THE INVENTION

In accordance with one embodiment of the invention, there is described An apparatus for aligning an instrument during a surgical procedure, the apparatus comprising a guide adapted for guiding an instrument during the surgical procedure; and alignment means coupled to the guide for aligning the guide along a translational path and first and second rotational paths.

In accordance with another embodiment of the invention, there is described an apparatus for aligning an instrument during an arthroplastic surgical procedure, the apparatus comprising a guide adapted for guiding an instrument during the arthroplastic procedure; a first assembly coupled to the guide adapted for positioning the guide along a translational path in controlled increments upon operation of the first assembly; a second assembly coupled to the guide adapted for positioning the guide along a first rotational path in controlled increments upon operation of the second assembly; and a third assembly coupled to the guide adapted for positioning the instrument guide along a second rotational path in controlled increments upon operation of the third assembly, whereby the guide is maintained in fixed position along the translational path and the first and second rotational paths upon termination of the operation of the first, second and third assemblies.

In accordance with another embodiment of the invention, there is described an apparatus for aligning a surgical cutting instrument during a surgical procedure along a translational path and first and second rotational paths, the apparatus comprising an instrument guide having an opening adapted for receiving the instrument; and an alignment guide having first, second and third assemblies coupled to the instrument guide for aligning the opening in controlled increments along the translational path and the first and second rotational paths; wherein the first, second and third assemblies each include a rotational component adapted for manipulating the instrument guide along the translational path and the first and second rotational paths upon rotation of the rotational component.

In accordance with another embodiment of the invention, there is described an apparatus for aligning an instrument during a surgical procedure, the apparatus comprising an instrument guide adapted for guiding the instrument during the surgical procedure; a first assembly adapted for aligning the instrument guide along a first rotational path, the first assembly including an internally threaded sleeve rotationally coupled to the instrument guide, a first pair of spaced apart rods slideably coupling a cross-member to the instrument guide, and a threaded first rod rotationally coupled at one end thereof to the sleeve and attached at another end thereof to the cross-member, whereby rotation of the sleeve effects translation of the cross-member thereby effecting manipulation of the instrument guide along the first rotational path; a second assembly adapted for aligning the instrument guide along a second rotational path, the second assembly including a housing supporting a rotatable plate including a first portion having a first gear and a second portion coupled to the instrument guide, and a rotatable second gear coupled to the first gear, whereby rotation of the second gear effects rotation of the plate thereby effecting manipulation of the instrument guide along the second rotational path; and a third assembly adapted for aligning the guide instrument along a translational path, the third assembly including a yoke, a second pair of spaced apart rods slideably coupling the yoke to the housing, and a second threaded rod rotatably coupled to the yoke and threadingly coupled to the housing, whereby rotation of the second threaded rod effects translation of the instrument guide relative to the yoke.

In accordance with another embodiment of the invention, there is described an apparatus for aligning a cutting instrument during a surgical procedure, the apparatus comprising a guide having an elongated slot adapted to receive a cutting instrument for resecting a patient's bone during a surgical procedure; a housing; a translational assembly coupled to the housing adapted for effecting distal-proximal adjustment of the guide; a first rotational assembly coupled to the housing adapted for effecting varus-valgus adjustment of the guide; the first rotational assembly is adapted to be releasably coupled to the guide and a second rotational assembly coupled to the guide adapted for effecting flexon-extension adjustment of the guide.

In accordance with another embodiment of the invention, there is described a method for aligning an instrument during a surgical procedure using an alignment apparatus comprising an instrument guide adapted for guiding the instrument during the surgical procedure; a first assembly adapted for aligning the instrument guide along a first rotational path, the first assembly including an internally threaded sleeve rotationally coupled to the instrument guide, a first pair of spaced apart rods slideably coupling a cross-member to the instrument guide, and a threaded first rod rotationally coupled at one end thereof to the sleeve and attached at another end thereof to the cross-member; a second assembly adapted for aligning the instrument guide along a second rotational path, the second assembly including a housing supporting a rotatable plate including a first portion having a first gear and a second portion coupled to the instrument guide, and a rotatable second gear coupled to the first gear; and a third assembly adapted for aligning the guide instrument along a translational path, the third assembly including a yoke, a second pair of spaced apart rods slideably coupling the yoke to the housing, and a second threaded rod rotatably coupled to the yoke and threadingly coupled to the housing; the method comprising rotating the sleeve to effect translation of the cross-member and manipulation of the instrument guide along the first rotational path, rotating the second gear to effect rotation of the plate and manipulation of the instrument guide along the second rotational path, and rotating the second threaded rod to effect translation of the instrument guide relative to the yoke.

BRIEF DESCRIPTION OF THE DRAWINGS

The above description, as well as further objects, features, and advantages of the present invention will be more fully understood with reference to the following detailed description of an apparatus for aligning an instrument during a surgical procedure, when taken in conjunction with the accompanying drawings, wherein.

DETAILED DESCRIPTION OF THE PREFERRED EMBODIMENTS

In describing the preferred embodiments of the subject matter illustrated and to be described with respect to the drawings, specific terminology will be resorted to for the sake of clarity. However, the invention is not intended to be limited to the specific terms so selected and is to be understood that each specific term includes all technical equivalence which operate in a similar manner to accomplish a similar purpose.

Figure 1:
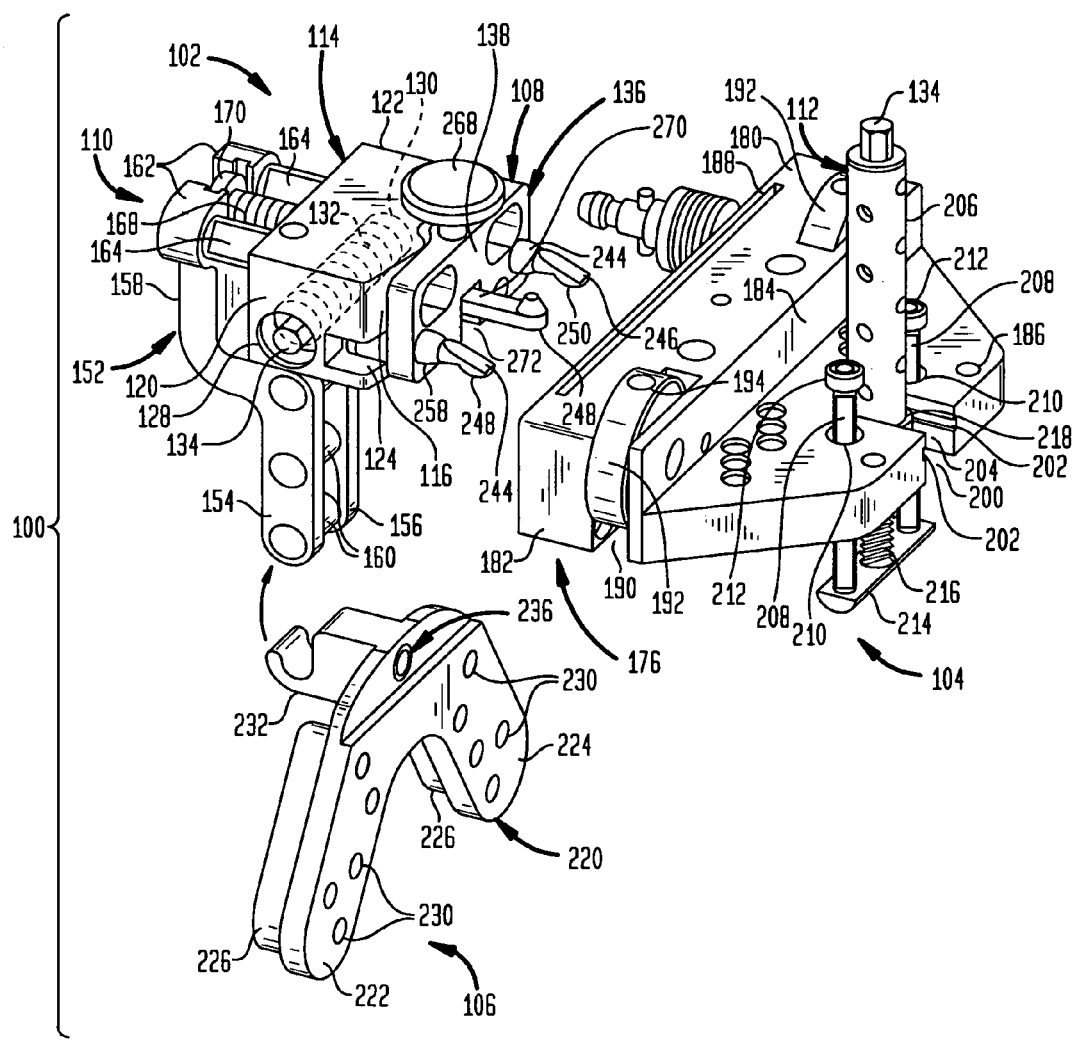
FIG. 1 is a perspective view of an unassembled resection guide adapted for aligning a cutting blade for resecting the distal femur.

Turning now to the drawings, wherein like reference numerals represent like elements, there is shown in FIG. 1 an alignment guide generally designated by reference numeral 100 adapted for femoral resection. The femoral alignment guide 100 includes an adjustment assembly 102, a femoral resection cutting guide 104 and a femoral fixation plate 106. As shown in FIG. 1, the components of the guide 100 are illustrated in an unassembled relationship. In this regard, the resection guide 104 and fixation plate 106 are to be releasably coupled to the adjustment assembly 102 during the arthroplastic surgery. As will be described hereinafter, the tibial alignment guide incorporates the use of the adjustment assembly 102, which is coupled to left-right tibial resection guides and a tibial fixation plate. Accordingly, the femoral and tibial resection guides and femoral and tibial fixation plates may be interchangeably coupled to the common adjustment assembly 102.

The femoral alignment guide 100 is provided with three assemblies to separately accommodate varus-valgus adjustment, resection level (distal-proximal) adjustment and flexion-extension adjustment. Specifically, the adjustment assembly 102 includes a varus-valgus adjustment assembly 108 and a resection level adjustment assembly 110, while a flexion-extension adjustment assembly 112 is coupled to the femoral and left-right tibial resection guides. Although the adjustment assemblies 108, 110, 112 are to be described as manually operated, it is contemplated that the adjustment assemblies can be coupled to a servo-motor and operated by a programmed computer.

Figure 3:
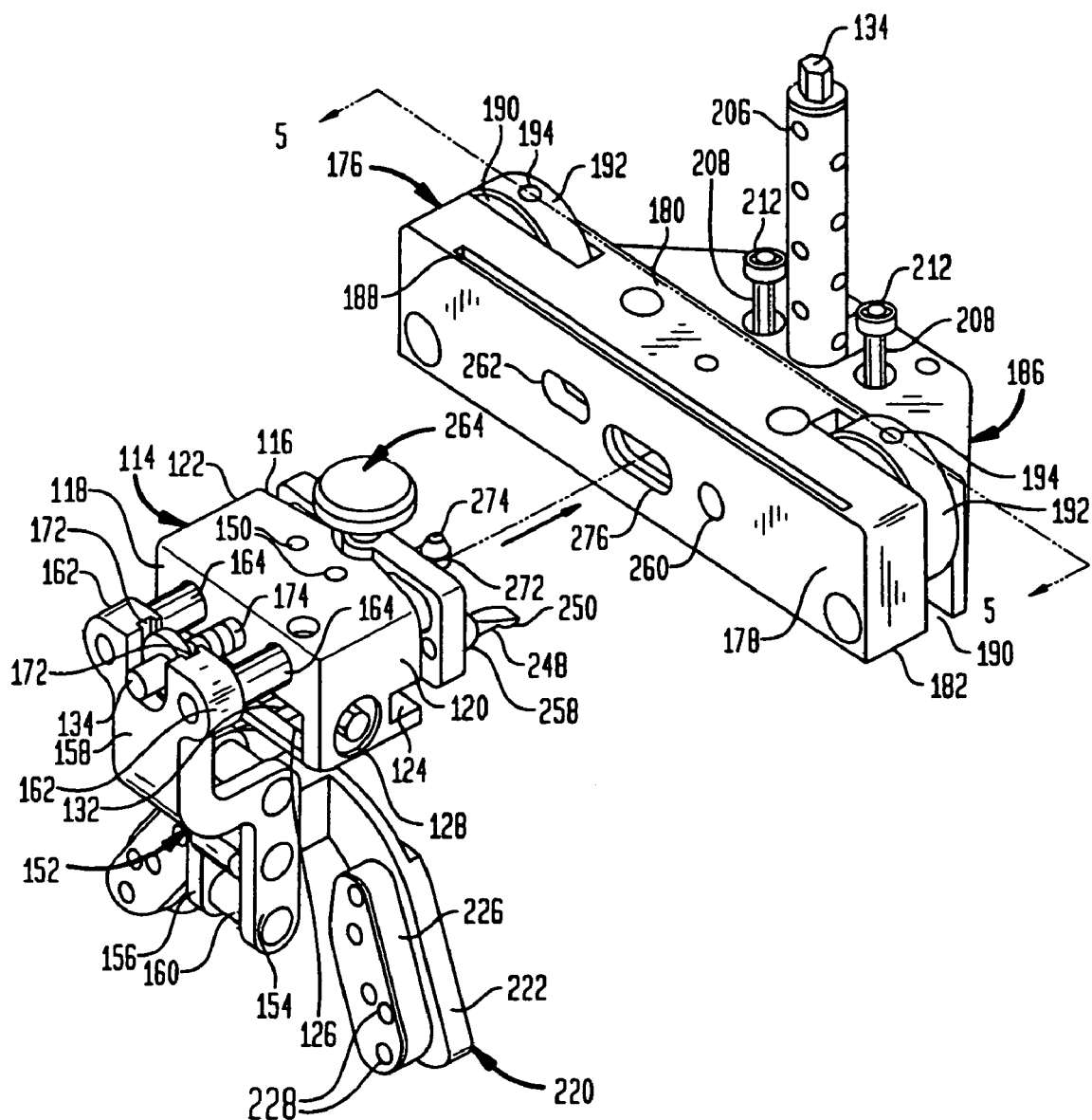
FIG. 3 is a perspective view of a partially assembled resection guide adapted for aligning a cutting blade for resecting the distal femur.

Referring to FIGS. 1 and 3, the varus-valgus adjustment assembly 108 includes an enclosed housing 114 having a front wall 116, a rear wall 118 and a pair of sidewalls 120, 122. The front wall 116 is provided with an elongated opening 124 which communicates with the interior of the housing 114 while extending into a portion of the sidewalls 120, 122. The rear wall 118 is provided with an opening 126 which opposes opening 124 in communication therewith. The sidewalls 120, 122 are each provided with a circular opening 128, 130 in longitudinal alignment with each other, while communication with the interior of the housing 114.

An elongated worm 132 is received within the housing 114 opposing opening 126. The ends of the worm 132 are rotationally journalled within openings 128, 130 provided in the sidewalls 120, 122. The ends of the worm 132 are provided with an engagement member 134 which enables rotation of the gear about its longitudinal axis within the housing 114. The engagement member 134, as shown, is in the nature of a polygonal shaped stud which can be received within a similarly shaped hand tool or coupled to a servo-motor to effect rotation of the worm 132.

Figure 4:
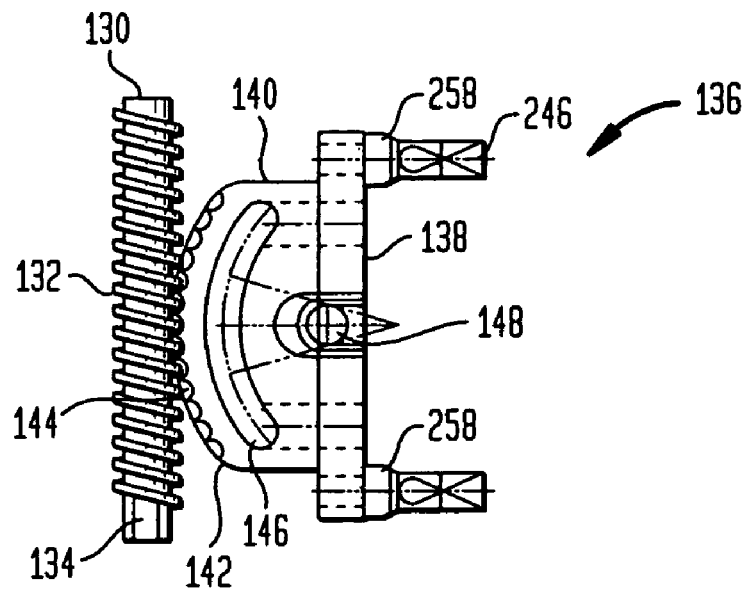
FIG. 4 is a top plan view of one component of an assembly for varus-valgus alignment of the resection guide and shows a worn interaction with teeth on a plate.

The varus-valgus adjustment assembly 108 further includes an L-shaped mounting bracket 136 as best shown in FIG. 4. The bracket 136 includes a planar front wall 138 and rearwardly extending planar bottom wall 140 arranged transverse thereto. The bottom wall 140 includes an arcuate-shaped leading edge 142 provided with a plurality of teeth 144. The teeth 144 are dimensioned so as to mesh with the worm 132. The L-shaped mounting bracket 136 is rotatably coupled to the worm, whereby rotation of the worm 132 causes rotation of the plate thereby causing rotation of the guide. An arcuate-shaped opening 146 is provided in the bottom wall 140 of the bracket 136 adjacent edge 142, generally having the same radius of curvature. A bore 148 is provided extending through a central portion of the front wall 138.

The bracket 136 is assembled into the housing 114 by inserting the bottom wall 140 through opening 124 until the teeth 144 mesh with worm 132. The bracket 136 is rotationally fixed within the housing 114 by a pair of spaced apart pins 150 which extend through the housing 114 and through the opening 146 in the bottom wall 140.

In the assembled relationship, the front wall 138 of the bracket 136 is positioned overlying the front wall 116 of the housing 114. As shown in FIG. 3, the front wall 116 slopes rearwardly towards the side walls 120, 122 at an angle from the central line of the front wall. This creates a space for the front wall 138 which allows the bracket 136 to pivot or rotate about its centerline to provide varus-valgus adjustment without interference with the housing 114.

The resection level adjustment assembly 110 includes a yoke 152 formed from a pair of spaced apart lower side arms 154, 156 and an upper solid connecting member 158. A plurality of transverse rods 160 are connected between the side arms 154, 156 at various spaced apart locations. The connecting member 158 supports a pair of ears 162 each having an opening into which there is fixed an elongated cylindrical shaft 164. As will become apparent, the shafts 164 need not be cylindrical, for example, other shapes such as square, polygonal, rectangular and the like are contemplated. Each of the shafts 164 are slidingly received within an opposing bore 166 of corresponding shape to the shaft 164 formed through the upper portion of the housing 114. A threaded adjustment rod 168 is provided with a circular flange 170 at one end thereof from which there extends an engagement member 134 which can be coupled to a hand tool or servo-motor. Flange 170 is rotationally captured between a pair of spaced apart aligned grooves 172 formed within the opposing inner sides of the ears 162. The threaded end of the adjustment rod 168 is threadingly received within a threaded bore 174 within the housing 114. As to be explained hereinafter, rotation of the adjustment rod 168 will affect resection level adjustment of the resection guide 104.

The resection guide 104 includes an enclosed housing 176 having a rear wall 178, a top wall 180, a bottom wall 182 and a front wall 184. A shelf 186 extends outwardly from the front wall 184. A narrow elongated slot 188 is formed extending longitudinally through the housing 176 adjacent rear wall 178. The slot 188 is adapted to receive a cutting instrument such as a surgical saw blade. The housing 176 includes a pair of spaced apart rectangular cutouts 190 into which there is rotationally mounted a cannulated wheel 192 each having a through bore 194 having an axis aligned with the diameter of the wheel.

Figure 5:
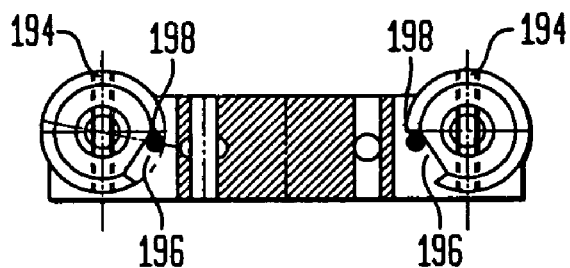
FIG. 5 is a cross-sectional view of a portion of the resection guide taken along line 5-5 in FIG. 3 illustrating cannulated wheels in a first orientation.
Figure 6:
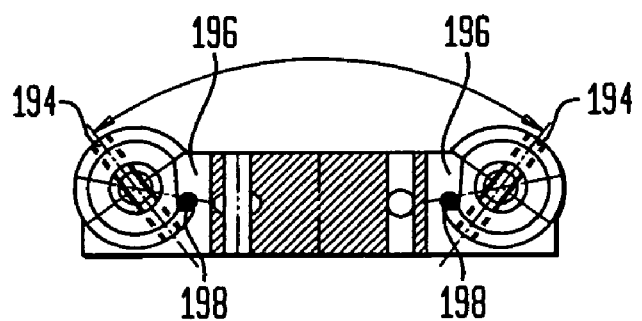
FIG. 6 is a cross-sectional view of FIG. 5 taken along line 5-5 with the cannulated wheels in a second orientation.

As shown in FIGS. 5 and 6, each of the cannulated wheels 192 are provided with a cutout 196 along a circumferential portion thereof. A pin 198 is attached to the housing 176 projecting into the cutouts 190 in operative alignment with cutouts 196 within the cannulated wheels 192. Accordingly, each wheel 192 may be rotated in a clockwise and counter-clockwise direction limited by the extent of the cutout 196. As the wheels 192 are rotated, the angular orientation of each of the through bores 194 can be manipulated between a vertical position as shown in FIG. 5 and an angular position as shown in FIG. 6. As explained hereinafter, the bores 194 are sized to receive a fixation pin (not shown).

The flexion-extension adjustment assembly 112 is coupled to the shelf 186 of the resection guide 104. The shelf 186 is provided with a forward elongated opening 200 having aligned grooves 202 formed within opposing sidewalls 204. The flexion-extension adjustment assembly 112 includes an elongated internally threaded sleeve 206 having an engagement member 134 at one end thereof which can be coupled to a hand tool or servo-motor. A pair of guide rods 208 are slidingly received within bores 210 extending through shelf 186 adjacent the sidewalls 204 forming the opening 200. One end of each of the rods 208 is provided with an enlarged stop member 212 having a size larger than that of the bore 210. The other end of the rods 208 are attached to an elongated cross-member 214 having a semi-circular cross-section. A threaded rod 216 has one end secured to the cross-member 214 between the guide rods 208. The other end of the rod 216 is threadingly received into the internally threaded sleeve 206. A circular flange 218 is attached to the sleeve 206, or integrally formed therewith, having a circumferential portion captured within the grooves 202. Accordingly, rotation of the sleeve 206 by means of the engagement member 134 effects longitudinal translation of the threaded rod 216 within the sleeve, which in turn, advances the cross member 214 while being guided by rods 208.

The femoral fixation plate 106 includes a C-shaped planar plate 220 formed by spaced apart legs 222, 224. A pin reinforcement guide 226 is secured to each of the legs 222, 224 having a plurality of holes 228 in alignment with corresponding holes 230 in the plate 220.

Figure 7:
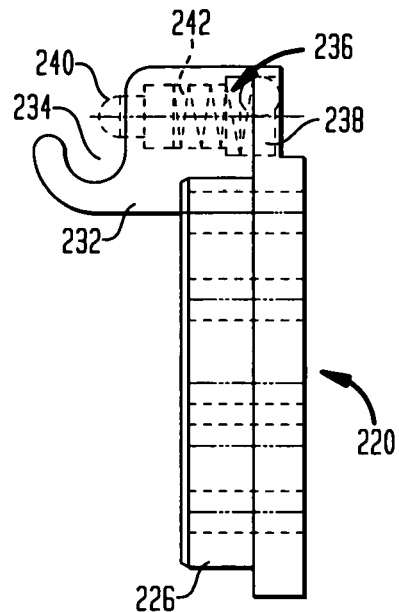
FIG. 7 is a side elevational view of a femoral fixation plate.

As best shown in FIG. 7, a hook-shaped projection 232 extends outwardly from the plate 220 between the legs 222, 224. The projection 232 is formed to provide an opening 234 which is restricted in size by a spring biased ball assembly 236. The ball assembly 236 is formed by a shaft 238 having a ball end 240 extending into the opening 234. The shaft is biased by an internal spring 242 to maintain the ball end 240 projecting outwardly to restrict the opening 234. The ball end 240 may be depressed inwardly into the projection 232 against the biasing force of spring 242 to enlarge the opening 234. As will be described hereinafter, the opening 234 is adapted to releasably capture one of the rods 160 on the yoke 152.

Figure 8:
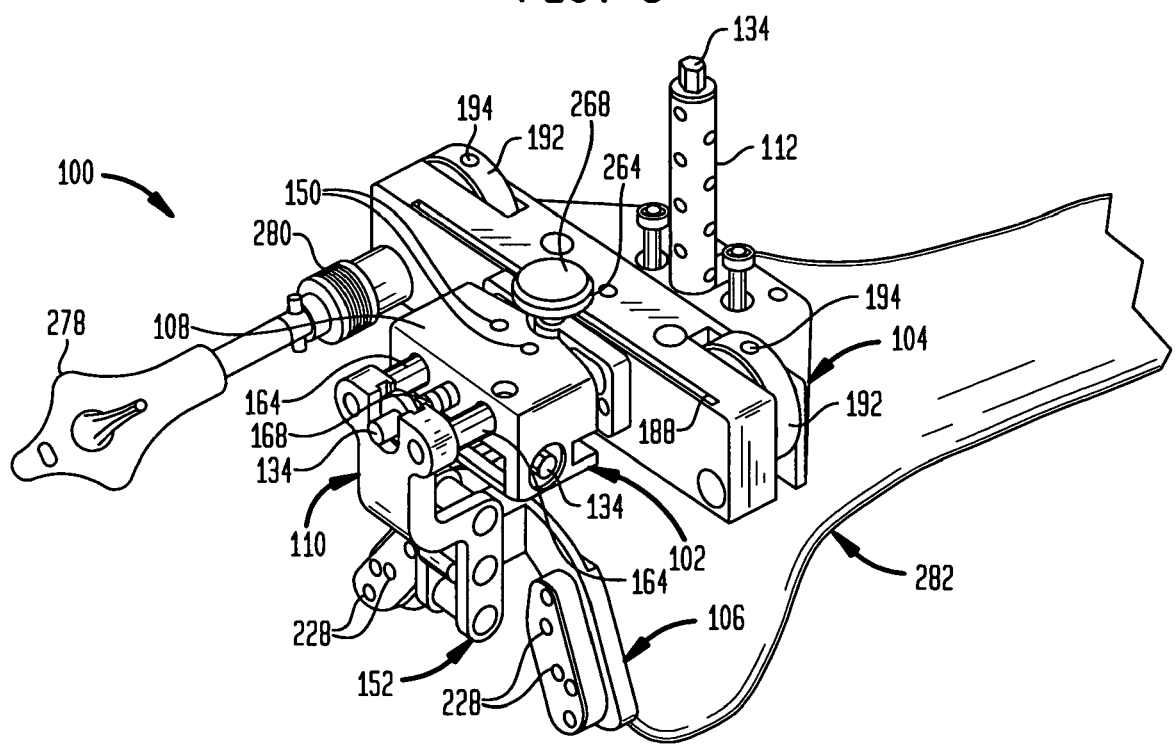
FIG. 8 is a perspective view of an assembled resection guide adapted for aligning a cutting blade for resecting the distal femur.

The femoral alignment guide 100 is assembled during various stages of the arthroplastic surgery. The final assembled form of the alignment guide 100 is shown in FIG. 8. By way of explanation, as shown in FIGS. 1 and 3, the femoral fixation plate 106 is rotationally coupled to the adjustment assembly 102. In this regard, the hooked-shaped projection 232 on the femoral fixation plate 106 is forced into engagement with one of the rods 160 on the yoke 152. The rod 160 will initially engage the ball end 240 of the ball assembly 236, displacing same to enable passage of the rod into the opening 234. The ball end 240 by virtue of being spring biased will retain rod 160 coupled to the hook-shaped projection 232. The height of the adjustment assembly 102 relative to the femur can be adjusted by attaching the femoral fixation plate 106 to a selected one of the rods 160. In the assembled relationship as shown in FIG. 3, the adjustment assembly 102 is rotational about the longitudinal axis of the rod 160 to which the femoral fixation plate 106 is coupled.

Turning to FIG. 1, the mounting bracket 136 is provided with a pair of positioning pins 244 extending outwardly from the front wall 138. The positioning pins 244 include an upper planar sloping surface 246 and an articulated bottom surface 248 having a bulbous end 250. The connection point of the positioning pins 244 to the bracket 236 is surrounded by a ferrule-like member 258, see FIG. 4.

The positioning pins 244 are adapted to be received within corresponding aligned openings within the resection guide 104. As best shown in FIG. 3, a circular opening 260 is spaced apart from an oblong opening 262, respectively aligned with the positioning pins 244. The provision of an oblong opening 262 facilitates alignment of the openings 260, 262 with the positioning pins 244. Insertion of the positioning pins 244 into their respective openings 260, 262 is also facilitated by the sloping top surface 246 and the bulbous end 250. The openings 260, 262 are sized to effectively receive the ferrule-like member 258 whereby the front wall 138 of the bracket 136 is brought into engagement with the rear wall 178 of the resection guide 104.

The adjustment assembly 102 is releasably coupled to the resection guide 104 by means of a locking assembly 264. The locking assembly 264 includes a spring biased shaft 266 which is slidingly received within bore 148 provided in the front wall 138 of the bracket 136. A knob 268 is attached to the extended exposed end of the shaft 266. An arm 270 is attached to the lower end of the shaft 266 extending outwardly from the bracket 136 through an opening 272. The free end of the arm 270 supports an upwardly extending projection 274 (See FIG. 3).

As shown in FIG. 3, the rear wall 178 of the resection guide 104 is provided with an oval-shaped opening 276 which receives the arm 270 on the locking assembly 264. A secondary opening (not shown) is formed within the housing 176 of the resection guide 104 in communication with opening 276. The formed opening is sized to receive the projection 274 thereby releasably attaching the adjustment assembly 102 to the resection guide 104. By depressing knob 268 downwardly, arm 270 will also be displaced downwardly to disengage the projection 274 from the opening within the housing 176.

The use of the femoral alignment guide 100 will be briefly described with reference to FIG. 8. In this regard, the alignment guide 100 is generally intended for any medical condition in which the use of computer-aided surgery may be appropriate, and where a reference to rigid anatomical structures, such as the femur or the tibia can be identified. As previously noted, one preferred application of the alignment guide 100 is in arthroplastic surgery to perform total knee replacement. The femoral alignment guide 100 is intended to be pinned to the distal portion of the femur for computer-aided alignment of the distal femoral cut. As to be described hereinafter, a tibial alignment guide is intended to be pinned to the proximal portion of the tibia for computer-aided alignment of the proximal tibia cut. However, the alignment guides can be coupled to the medial and lateral sides of the tibia and femur. In this regard, the alignment guide is modular in construction and can be used in both the femur and tibia configurations. While the adjustment assembly 102 is universal, the resection cutting guide and fixation plates are assembled depending on the bone undergoing treatment.

As shown in FIG. 8, the femoral fixation plate 106 is pivotably attached to the adjustable assembly 102. In turn the adjustable assembly 102 is mounted to the resection cutting guide 104. The assembly of the femoral alignment guide 100 is accomplished in the manner as previously described. A tracker 278 is attached to the resection cutting guide 104 by means of tracker adaptor 280. The tracker 278, by way of example, is an electronic LED device which is visible to a camera providing two-way communication. The tracker 278 is used in conjunction with a navigation system which allows correct positioning and orientation of the implants. One such navigation system for use in arthroplastic surgery is known as the Stryker Knee Navigation System, which is available from Stryker Howmedica Osteonics of Allendale, N.J. The operation of the navigation system and tracker 278 in conjunction with the use of a femoral and tibial alignment guide is more fully described in the Stryker Navigation System User Manual, Knee Navigation V. 1.1, and incorporated in its entirety by reference.

The femoral fixation plate 106 is pressed onto the distal condyles of the femur 282. Initially, the tracker 278 is aligned with the sensors in the navigation system by rotating the tracker adapted 280 on the resection cutting guide 104. Preferably, the femoral alignment guide 100 can be secured to the femur 282 using pins (not shown) inserted through one or more of the holes 228, 230 in the femoral fixation plate 106.

The varus-valgus angle, flexion extension angle and resection level are now adjusted using the assemblies 108, 110 and 112. The adjustment using one of the assemblies 108, 110, 112 will not effect the alignment based on the use of another assembly. Specifically, the varus-valgus angle is adjusted by rotating worm 132 using any suitable implement which is operative for rotating the engagement member 134. As the worm 132 is rotated within housing 114, the varus-valgus mounting bracket 136 will rotate about its central line by virtue of pins 150 extending through the arcuate-shaped opening 146 within the bottom wall 140 thereof. As the mounting bracket 136 rotates, a corresponding rotation of the resection guide 104 will occur thereby providing varus-valgus alignment. The proper varus-valgus angle may be determined using the tracker 278 and the navigation system.

The use of a meshed gear-type arrangement in the varus-valgus adjustment assembly 108 allows for the precise controlled manipulation of the resection cutting guide 104 in controlled increments. That is, for each rotation of worm 132, a predetermined angular rotation will be imparted to the resection cutting guide 104 providing for continuously variable adjustment. By selecting the design of the worm 132 and teeth 144 on the mounting bracket 136, precision control of aligning the resection guide for varus-valgus angle can be accomplished. Based upon the foregoing construction of the varus-valgus adjustment assembly 108, the resection guide 104 is maintained in its proper angular orientation by the adjustment assembly once rotation of the worm 132 is terminated. Accordingly, there is no requirement for a secondary clamping or locking assembly, such as a cam lock, to maintain the proper varus-valgus angle of the resection guide 104 during any period of the adjustment process.

The flexion-extension angle is adjusted using the flexion-extension adjustment assembly 112, which is coupled to the resection cutting guide 104. Sleeve 206 is rotated by a suitable tool which is attached to the engagement member 134. As the sleeve 206 is rotated, the cross-member 214 which is attached to the thread rod 216 is advanced longitudinally while being guided by the spaced apart guide rods 208, providing continuously variable adjustment. The cross member 214 will press against the femur 282 which results in rotation of the resection cutting guide 104 about the specific rod 160 to which the femoral fixation plate 106 is coupled via the hook shaped projection 232. The flexion-extension angle can be monitored using the tracker 278 coupled with the navigation system in a similar manner as monitoring the varus-valgus angle adjustment. Each rotation of the sleeve 206 will result in a predetermined linear advancement of the cross-member 214 in controlled increments. This advancement is controlled by the pitch of the threads on the threaded rod 216 and the threads on the internally threaded sleeve 206. As a result of the threaded engagement between the rod 216 and sleeve 206, the cross-member 214 will maintain its position upon termination of rotation of the sleeve. For those reasons as previously described, this avoids the necessity of a clamping or locking assembly to maintain the resection guide 104 in proper flexion-extension angular adjustment.

The resection level, i.e., proximal-distal, for the resection guide 104 is adjusted using the resection level adjustment assembly 110. The resection level is accordingly adjusted by rotation of the threaded adjustment rod 168 by attaching a suitable implement to the engagement member 134 providing continuous variable adjustment. As the threaded rod 168 is rotated, the housing 114 of the adjustment assembly 102 is displaced in controlled increments away from the yoke 152 while being guided by the pair of spaced apart shafts 164. Due to the threaded engagement of the threaded rod 168 with the housing 114, the resection level of the resection cutting guide 104 can be controlled, as well as avoiding the need for a secondary locking or clamping assembly.

After the resection cutting guide 104 has been properly adjusted in varus-valgus angle, flexion-extension angle and resection level, a pin (not shown) is inserted into the bore 194 of the cannulated wheels 192. The pins are aligned perpendicular to the femur 282 by rotating the cannulated wheels 192. The pins are then attached to the femur 282 to fixate the resection cutting guide 104. If required, additional cross-pins may be used in openings extending through the resection cutting guide 104.

The pins securing the femoral fixation plate 106 are removed to free the adjustment assembly 102 from the femur 282. The adjustment assembly 102 is detached from the resection cutting guide 104 by depressing knob 268 in order to release the locking assembly 264. Subsequently, a suitable surgical instrument such as cutting blade may be inserted into the slot 188 to effect resection of the femur 282.

Figure 2:
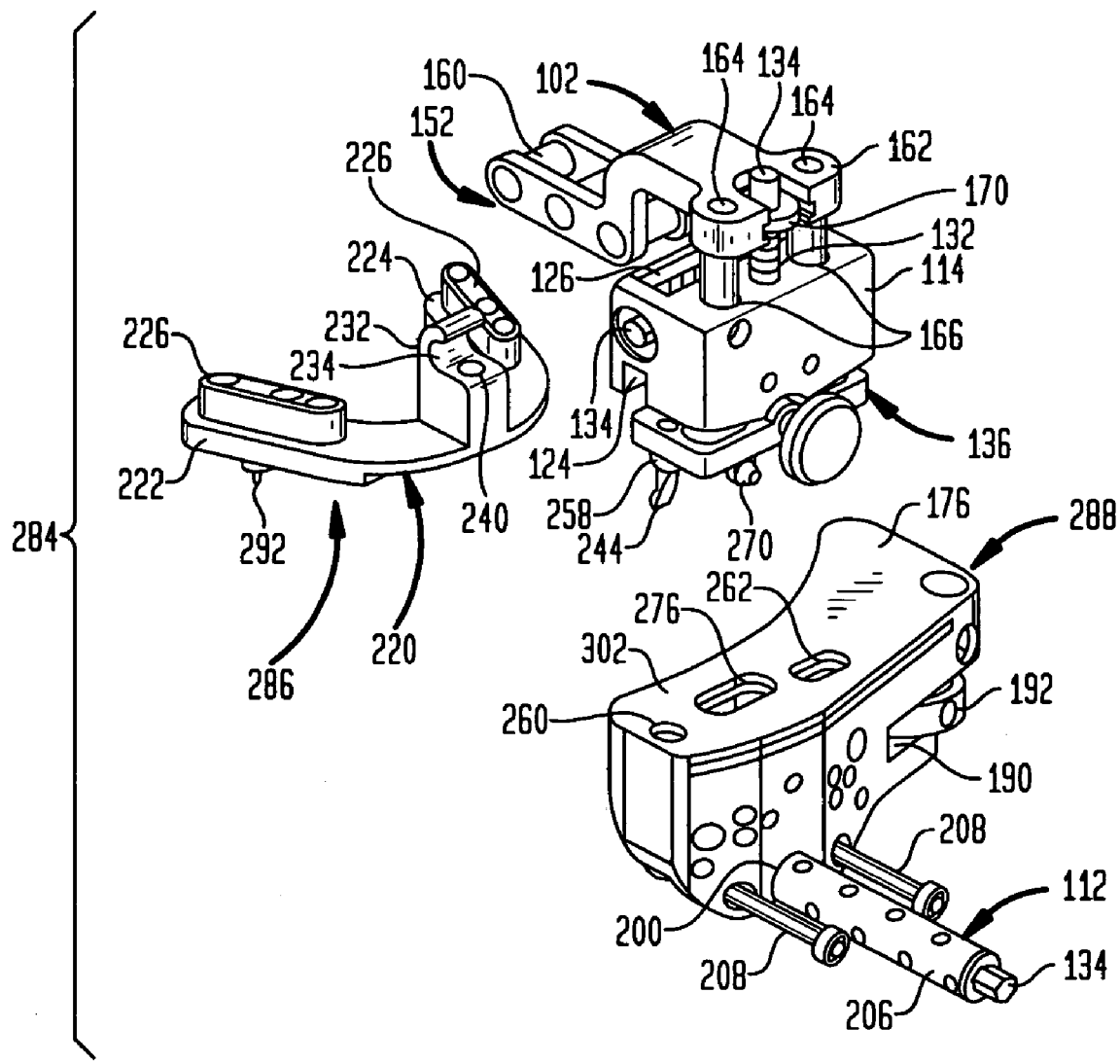
FIG. 2 is a perspective view of an unassembled resection guide adapted for aligning a cutting blade for resecting the proximal tibia.
Figure 9:
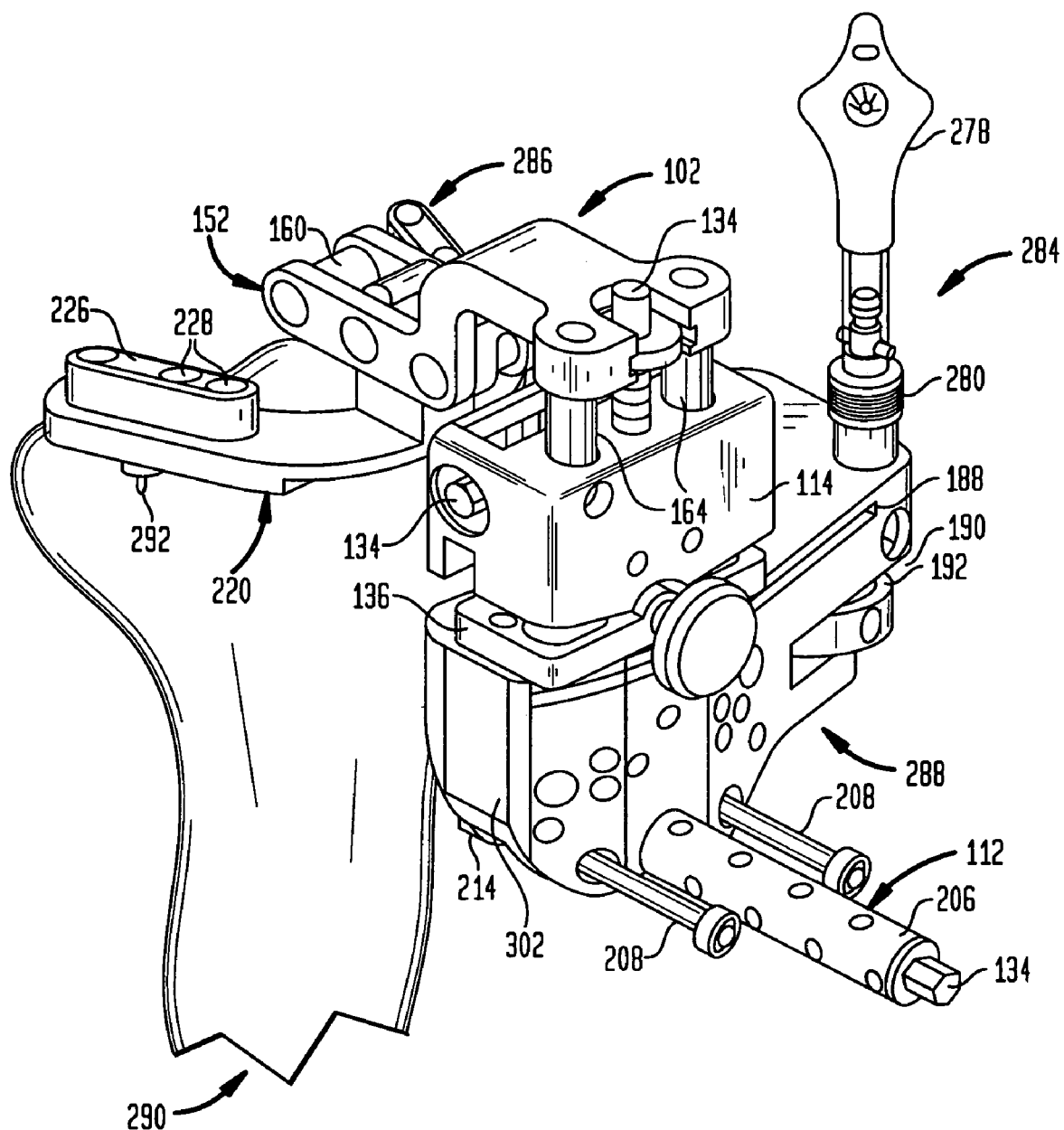
FIG. 9 is a perspective view of an assembled resection guide adapted for aligning a cutting blade for resecting the proximal tibia.

Referring to FIGS. 2 and 9, there is shown the construction of a tibial alignment guide generally designated by reference numeral 284. The tibial alignment guide 284 includes a common adjustment assembly 102, a tibial fixation plate 286 and a resection cutting guide 288. Due to the anatomical nature of the proximal tibia, it is generally preferred to provide a separate resection cutting guide 288 for the left and right tibia. In this regard, the resection cutting guide 288 is illustrated as a right tibia resection guide, the left tibia resection guide being a mirror image thereof.

Figure 10:
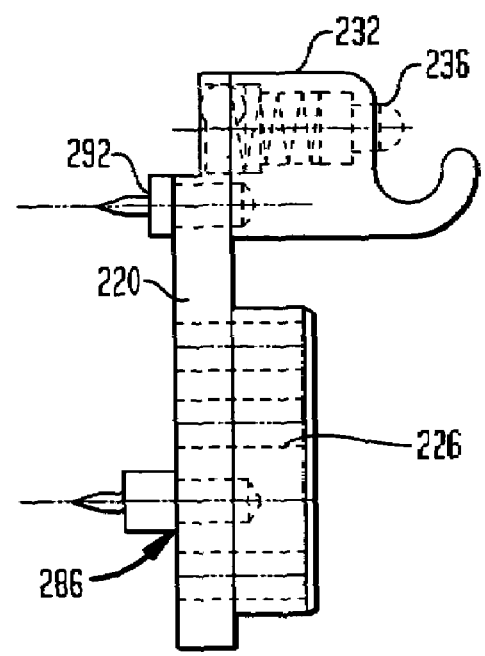
FIG. 10 is a side elevational view of the tibial fixation plate.
Figure 11:
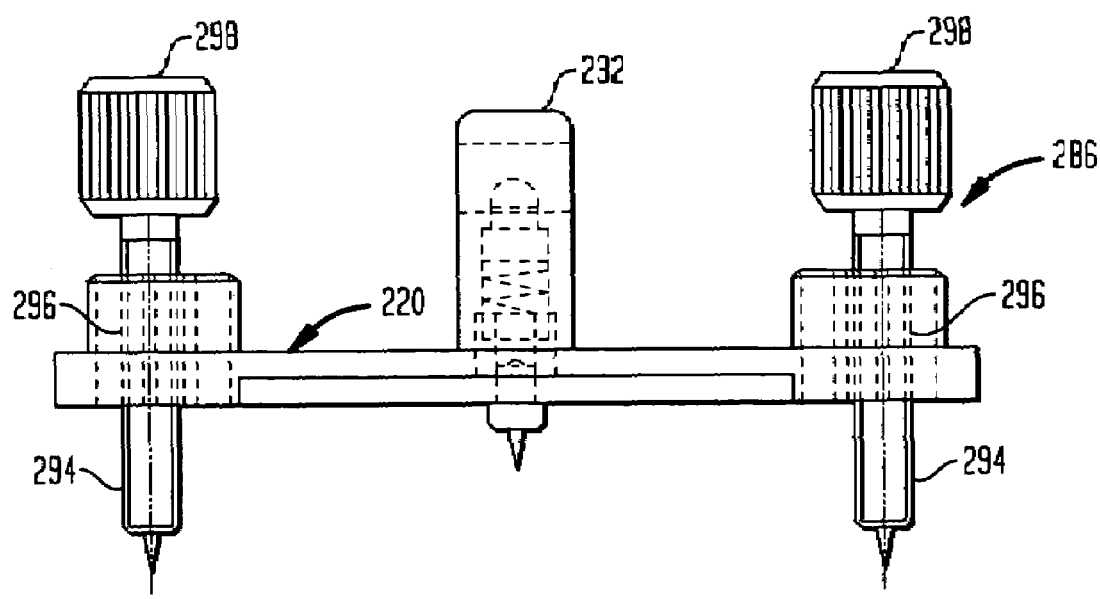
FIG. 11 is a top-plan view of a tibial fixation plate.

The tibial fixation plate 286 as also shown in FIG. 10 is constructed in a similar manner as the femoral fixation plate 106. In this regard, the tibial fixation plate 286 includes a C-shaped plate 220 formed by a pair of spaced apart legs 222, 224, supporting pin reinforcement guides 226. The shape of the plate 220 is altered to accommodate mounting of the plate to the tibia 290 as shown in FIG. 9. By way of example, one or more projecting pins 292 of varying length can be attached to the plate 220 for supporting the fixation plate onto the proximal compartments of the tibia 290. The tibia fixation plate 286 is rotationally coupled to the yoke 152 as previously described with respect to the femoral fixation plate 106. In an alternative embodiment as shown in FIG. 11, the tibial fixation plate 286 is provided with a plurality of adjustable pins 294 which are threadingly received within the pin reinforcement guided 226. The pins 294 include a threaded shaft 296, which upon rotation by knob 298, advances the pointed end 300 to adjust the length of a respective pin 294.

The tibial resection cutting guide 288 is generally similar in construction to the femoral resection cutting guide 104, but for the inclusion of only a single cannulated wheel 192. By way of further description, the tibial resection cutting guide 288 is provided with a housing 302 supporting the elongated slot 188 adjacent rear wall 178. A single cannulated wheel 192 is rotationally supported within cutout 190. The flexion-extension adjustment assembly 112 is coupled to the forward end of the housing 302 in the manner as previously described with respect to the femoral resection cutting guide 104. As shown, the flexion-extension adjustment assembly 112 is arranged off center, e.g., on the left side of the housing 302 while the cannulated wheel 192 is positioned within the right side of the housing. The construction of the left tibial resection cutting guide would reverse the positions of the flexion-extension adjustment assembly 112 and cannulated wheel 192.

The tibial resection cutting guide 288 is mounted to the adjustment assembly 202 in the manner as previously described with respect to the femoral resection cutting guide 104. The assembled tibial alignment guide 284 is shown in FIG. 9. The tibial resection cutting guide 288 is similarly positioned using a tracker 178 in operative association with a navigation system. After fixing the tibial fixation plate 286 to the proximal compartments of the tibia, the resection cutting guide 288 is adjusted in varus-valgus angle, flexion-extension angle and resection level. This is accomplished using the varus-valgus adjustment assembly 108, resection level adjustment assembly 110, and flexion-extension adjustment assembly 112 as previously described.

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

The invention claimed is:

1. An apparatus for aligning a cutting instrument during a surgical procedure along a translational path and first and second rotational paths, said apparatus comprising an instrument guide having an opening for receiving said instrument; and an alignment guide having first and second assemblies removably coupled to, and a third assembly fixedly attached to said instrument guide for aligning said opening in continuous variable adjustments along each of said translational path and said first and second rotational paths; each of said first, second and third assemblies including a rotational component adapted for manipulating said instrument along said translational path and said first and second rotational paths upon rotation of said rotational component.

2. The apparatus of claim 1, wherein said first and second assemblies are coupled to a housing.

3. The apparatus of claim 2, wherein said first assembly comprises a yoke, a pair of spaced apart rods slideably coupling said yoke to said housing, and a threaded rod rotatably coupled to said yoke and threadingly coupled to said housing, whereby rotation of said rod causes translation of said guide relative to said yoke.

4. The apparatus of claim 3, wherein said yoke includes a pair of spaced apart arms and at least one rod transversely attached therebetween.

5. The apparatus of claim 4, further including a fixation plate adapted to be fixed to a patient's bone during the surgical procedure, said fixation plate pivotably coupled to said rod.

6. The apparatus of claim 2, wherein said second assembly comprises a plate having a first portion coupled to said guide and a second portion rotatably coupled to a worm within said housing, whereby rotation of said worm causes rotation of said plate thereby causing rotation of said guide.

7. The apparatus of claim 6, further including coupling means for releasably coupling said first portion of said second assembly to said guide.

8. The apparatus of claim 6, wherein said second portion of said plate comprises a wall having an arcuate shaped opening, and at least one pin received within said housing and having a portion captured within said opening.

9. The apparatus of claim 8, wherein said wall includes a plurality of teeth meshed with said worm.

10. The apparatus of claim 1, wherein said third assembly comprises an internally threaded sleeve rotatably coupled to said guide, a pair of spaced apart rods slideably coupling a cross-member to said guide, and a threaded rod threadingly coupled at one end thereof within said sleeve and attached to said cross-member at another end thereof, whereby rotation of said sleeve causes translation of said cross-member thereby causing rotation of said guide.

11. The apparatus of claim 10, wherein said guide includes a shelf having an opening, said sleeve rotational coupled to said shelf within said opening.

12. The apparatus of claim 1, wherein said guide includes a slotted opening adapted to receive the surgical instrument.

13. An apparatus for aligning an instrument during an arthroplastic surgical procedure, said apparatus comprising a guide adapted for guiding an instrument during said arthroplastic procedure;

a first assembly coupled to said guide adapted for positioning said guide along a translational path in continuous variable adjustments upon operation of said first assembly;

a second assembly coupled to said guide adapted for positioning said guide along a first rotational path in continuous variable adjustments upon operation of said second assembly; and a third assembly attached to said guide adapted for positioning said instrument guide along a second rotational path in continuous variable adjustments upon operation of said third assembly, whereby said guide is maintained in fixed position along said translational path and said first and second rotational paths upon termination of the operation of said first, second and third assemblies.

14. The apparatus of claim 13, wherein said first and second assemblies are coupled to a housing.

15. The apparatus of claim 14, wherein said first assembly comprises a yoke, a pair of spaced apart rods slideably coupling said yoke to said housing, and a threaded rod rotatably coupled to said yoke and threadingly coupled to said housing, whereby rotation of said rod causes translation of said guide relative to said yoke.

16. The apparatus of claim 15, wherein said yoke includes a pair of spaced apart arms and at least one rod transversely attached therebetween.

17. The apparatus of claim 16, further including a fixation plate adapted to be fixed to a patient's bone during the surgical procedure, said fixation plate pivotably coupled to said rod.

18. The apparatus of claim 14, wherein said second assembly comprises a plate having a first portion coupled to said guide and a second portion rotatably coupled to a worm within said housing, whereby rotation of said worm causes rotation of said plate thereby causing rotation of said guide.

19. The apparatus of claim 18, further including coupling means for releasably coupling said first portion of said second assembly to said guide.

20. The apparatus of claim 18, wherein said second portion of said plate comprises a wall having an arcuate shaped opening, and at least one pin received within said housing and having a portion captured within said opening.

21. The apparatus of claim 20, wherein said wall includes a plurality of teeth meshed with said worm.

22. The apparatus of claim 13, wherein said third assembly comprises an internally threaded sleeve rotatably coupled to said guide, a pair of spaced apart rods slideably coupling a cross-member to said guide, and a threaded rod threadingly coupled at one end thereof within said sleeve and attached to said cross-member at another end thereof, whereby rotation of said sleeve causes translation of said cross-member thereby causing rotation of said guide.

23. The apparatus of claim 22, wherein said guide includes a shelf having an opening, said sleeve rotational coupled to said shelf within said opening.

24. The apparatus of claim 13, wherein said guide includes a slotted opening adapted to receive the surgical instrument.

25. An apparatus for aligning a surgical cutting instrument during a surgical procedure along a translational path and first and second rotational paths, said apparatus comprising an instrument guide having an opening adapted for receiving said instrument; and an alignment guide having first and second assemblies coupled to and said third assembly attached to said instrument guide for aligning said opening in continuous variable adjustments along said translational path and said first and second rotational paths; wherein said first, second and third assemblies each include a rotational component adapted for manipulating said instrument guide along said translational path and said first and second rotational paths upon rotation of said rotational component.

26. The apparatus of claim 25, wherein said first and second assemblies are coupled to a housing.

27. The apparatus of claim 26, wherein said first assembly comprises a yoke, a pair of spaced apart rods slideably coupling said yoke to said housing, and a threaded rod rotatably coupled to said yoke and threadingly coupled to said housing, whereby rotation of said rod causes translation of said guide relative to said yoke.

28. The apparatus of claim 27, wherein said yoke includes a pair of spaced apart arms and at least one rod transversely attached therebetween.

29. The apparatus of claim 28, further including a fixation plate adapted to be fixed to a patient's bone during the surgical procedure, said fixation plate pivotably coupled to said rod.

30. The apparatus of claim 26, wherein said second assembly comprises a plate having a first portion coupled to said guide and a second portion rotatably coupled to a worm within said housing, whereby rotation of said worm causes rotation of said plate thereby causing rotation of said guide.

31. The apparatus of claim 30, further including coupling means for releasably coupling said first portion of said second assembly to said guide.

32. The apparatus of claim 30, wherein said second portion of said plate comprises a wall having an arcuate shaped opening, and at least one pin received within said housing and having a portion captured within said opening.

33. The apparatus of claim 32, wherein said wall includes a plurality of teeth meshed with said worm.

34. The apparatus of claim 25, wherein said third assembly comprises an internally threaded sleeve rotatably coupled to said guide, a pair of spaced apart rods slideably coupling a cross-member to said guide, and a threaded rod threadingly coupled at one end thereof within said sleeve and attached to said cross-member at another end thereof, whereby rotation of said sleeve causes translation of said cross-member thereby causing rotation of said guide.

35. The apparatus of claim 34, wherein said guide includes a shelf having an opening, said sleeve rotational coupled to said shelf within said opening.

36. An apparatus for aligning an instrument during a surgical procedure, said apparatus comprising an instrument guide adapted for guiding said instrument during said surgical procedure; a first assembly adapted for aligning said instrument guide along a first rotational path, said first assembly including an internally threaded sleeve rotationally coupled to said instrument guide, a first pair of spaced apart rods slideably coupling a cross-member to said instrument guide, and a threaded first rod rotationally coupled at one end thereof to said sleeve and attached at another end thereof to said cross-member, whereby rotation of said sleeve effects translation of said cross-member thereby effecting manipulation of said instrument guide along said first rotational path; a second assembly adapted for aligning said instrument guide along a second rotational path, said second assembly including a housing supporting a rotatable plate including a first portion having a first gear and a second portion coupled to said instrument guide, and a rotatable second gear coupled to said first gear, whereby rotation of said second gear effects rotation of said plate thereby effecting manipulation of said instrument guide along said second rotational path; and a third assembly adapted for aligning said guide instrument along a translational path, said third assembly including a yoke, a second pair of spaced apart rods slideably coupling said yoke to said housing, and a second threaded rod rotatably coupled to said yoke and threadingly coupled to said housing, whereby rotation of said second threaded rod effects translation of said instrument guide relative to said yoke.

37. The apparatus of claim 36, wherein said guide includes a slotted opening adapted to receive the instrument.

38. The apparatus of claim 36, wherein said yoke includes a pair of spaced apart arms and at least one rod transversely attached therebetween.

39. The apparatus of claim 38, further including a fixation plate adapted to be fixed to a patient's bone during the surgical procedure, said fixation plate pivotably coupled to said rod.

40. The apparatus of claim 36, wherein said guide includes a shelf having an opening, said sleeve rotational coupled to said shelf within said opening.

41. An apparatus for aligning a cutting instrument during a surgical procedure, said apparatus comprising a guide having an elongated slot adapted to receive a cutting instrument for resecting a patient's bone during a surgical procedure; a housing;
  a translational assembly coupled to said housing adapted for effecting distal-proximal adjustment of said guide;
  a first rotational assembly coupled to said housing adapted for effecting varus-valgus adjustment of said guide, said first rotational assembly adapted to be releasably coupled to said guide; and
  a second rotational assembly attached to said guide adapted for effecting flexon-extension adjustment of said guide, wherein each of said assemblies include a member adapted for causing continuous variable adjustment of said guide upon rotation of said member.

42. The apparatus of claim 41, wherein said translational assembly and said first and second rotational assemblies are constructed to align said guide in controlled increments.

43. The apparatus of claim 41, wherein said member in said translational assembly compromises a threaded rod rotatably coupled to a yoke and threadingly coupled to said housing, said yoke supported by a pair of spaced apart rods slideably coupling said yoke to said housing, whereby rotation of said rod causes translation of said guide.

44. The apparatus of claim 41, wherein said member in said first rotational assembly comprises a worm within said housing, said first rotational assembly further including a plate having a first portion coupled to said guide and a second portion rotatably coupled to said worm within said housing, whereby rotation of said worm causes rotation of said plate thereby causing rotation of said guide.

45. The apparatus of claim 44, wherein said second portion of said plate comprises a wall having an arcuate shaped opening, and at least one pin received within said housing and having a portion captured within said opening.

46. The apparatus of claim 41, wherein said member in said second rotational assembly comprises a threaded rod, said second rotational assembly further including an internally threaded sleeve rotatably coupled to said guide, a pair of spaced apart rods slideably coupling a cross-member to said guide, and said threaded rod threadingly coupled at one end thereof within said sleeve and attached to said cross-member at another end thereof, whereby rotation of said sleeve causes translation of said cross-member thereby causing rotation of said guide.

47. The apparatus of claim 46, wherein said guide includes a shelf having an opening, said sleeve rotational coupled to said shelf within said opening.

48. A method for aligning an instrument during a surgical procedure using an alignment apparatus comprising an instrument guide adapted for guiding said instrument during said surgical procedure; a first assembly adapted for aligning said instrument guide along a first rotational path, said first assembly including an internally threaded sleeve rotationally coupled to said instrument guide, a first pair of spaced apart rods slideably coupling a cross-member to said instrument guide, and a threaded first rod rotationally coupled at one end thereof to said sleeve and attached at another end thereof to said cross-member; a second assembly adapted for aligning said instrument guide along a second rotational path, said second assembly including a housing supporting a rotatable plate including a first portion having a first gear and a second portion coupled to said instrument guide, and a rotatable second gear coupled to said first gear; and a third assembly adapted for aligning said guide instrument along a translational path, said third assembly including a yoke, a second pair of spaced apart rods slideably coupling said yoke to said housing, and a second threaded rod rotatably coupled to said yoke and threadingly coupled to said housing; said method comprising rotating said sleeve to effect translation of said cross-member and manipulation of said instrument guide along said first rotational path, rotating said second gear to effect rotation of said plate and manipulation of said instrument guide along said second rotational path, and rotating said second threaded rod to effect translation of said instrument guide relative to said yoke.

49. The method of claim 48, further including attaching a fixation plate to a patient's bone, and pivotably coupling said fixation plate to said yoke.

\* \* \* \* \*

UNITED STATES PATENT AND TRADEMARK OFFICE
CERTIFICATE OF CORRECTION

| | | |
|---|---|---|
| PATENT NO. | : 7,309,339 B2 | Page 1 of 1 |
| APPLICATION NO. | : 10/766789 | |
| DATED | : December 18, 2007 | |
| INVENTOR(S) | : Michael J. Cusick and Jens Rüber | |

It is certified that error appears in the above-identified patent and that said Letters Patent is hereby corrected as shown below:

Specification Col. 4, Line 9, before "interaction", "worn" should read --worm--.

Specification Col. 9, Line 22, before "projection", "hook shaped" should read --hook-shaped--.

Signed and Sealed this

Ninth Day of December, 2008

JON W. DUDAS
*Director of the United States Patent and Trademark Office*